(12) United States Patent
Freschl et al.

(10) Patent No.: US 12,343,193 B1
(45) Date of Patent: Jul. 1, 2025

(54) SYSTEMS AND METHODS FOR A HYBRID ANALOG-DIGITAL STETHOSCOPE

(71) Applicant: Eko Health, Inc., Emeryville, CA (US)

(72) Inventors: Dan Freschl, Albany, CA (US); Michael Childs, Palm Springs, CA (US); Subramaniam Venkatraman, Emeryville, CA (US); Shanmugam Muruga Palaniappan, Berkeley, CA (US); Theo Brower, Berkeley, CA (US)

(73) Assignee: EKO HEALTH, INC., Emeryville, CA (US)

( * ) Notice: Subject to any disclaimer, the term of this patent is extended or adjusted under 35 U.S.C. 154(b) by 0 days.

(21) Appl. No.: 18/908,589

(22) Filed: Oct. 7, 2024

(51) Int. Cl.
*A61B 7/04* (2006.01)
*H04R 1/46* (2006.01)
*H04R 3/00* (2006.01)

(52) U.S. Cl.
CPC ............ *A61B 7/04* (2013.01); *H04R 1/46* (2013.01); *H04R 3/00* (2013.01); *H04R 2430/01* (2013.01)

(58) Field of Classification Search
CPC ... A61B 7/04; H04R 1/46; H04R 3/00; H04R 2430/01
See application file for complete search history.

(56) References Cited

U.S. PATENT DOCUMENTS

| | | | | |
|---|---|---|---|---|
| 3,247,324 A * | 4/1966 | Cefaly | ............ | A61B 7/02 D24/134 |
| 3,539,724 A * | 11/1970 | Keesee | ............ | H03F 3/183 381/98 |
| 4,071,694 A * | 1/1978 | Pfeiffer | ............ | A61B 7/02 381/67 |
| 5,774,563 A * | 6/1998 | DesLauriers | ............ | A61B 7/026 381/67 |
| 6,002,777 A * | 12/1999 | Grasfield | ............ | A61B 7/04 D24/134 |
| 2015/0297171 A1 * | 10/2015 | Thiagarajan | ............ | A61B 5/0205 381/300 |
| 2019/0274656 A1 * | 9/2019 | Pande | ............ | A61B 7/04 |
| 2024/0138781 A1 * | 5/2024 | Freschl | ............ | A61B 5/0006 |

* cited by examiner

*Primary Examiner* — Andrew Sniezek
(74) *Attorney, Agent, or Firm* — McCoy Russell LLP

(57) ABSTRACT

Methods and systems for a hybrid analog-digital stethoscope is herein provided. In one example, an electronic stethoscope comprises a chestpiece including a sound collecting interface and a plurality of electronic components, wherein the plurality of electronic components includes one or more microphones and one or more speakers; an output tube coupled to the chestpiece via a connector comprising a mode switching port, wherein the output tube, when the mode switching port is in a first position for digital mode, is in acoustic communication with the one or more speakers and, when the mode switching port is in a second position for analog mode, is in acoustic communication with the sound collecting interface.

20 Claims, 13 Drawing Sheets

SYSTEMS AND METHODS FOR A HYBRID ANALOG-DIGITAL STETHOSCOPE

FIELD

The present description relates generally to methods and systems for digital stethoscopes, such as hybrid analog-digital stethoscopes.

BACKGROUND/SUMMARY

Auscultation, the process of listening to internal sounds of a body, has historically been performed with an acoustic stethoscope. As one example, the acoustic stethoscope may include a two-sided chestpiece attached to hollow tubing that branches to the practitioner's ears. Bodily sounds are generally in a range of frequencies between 20 and 2500 Hz. A diaphragm on one side of the chestpiece may transmit relatively high frequency sounds to the earpieces, with respect to the range of frequencies of bodily sounds, or a bell on the other side of the chestpiece may transmit relatively low frequency sounds to the earpieces. Thus the diaphragm side may be more suited towards pulmonary auscultation while the bell side may be more suited towards cardiac auscultation, though there may be overlap between usages. However, such acoustic stethoscopes are unable to digitize sounds that can be easily analyzed and shared electronically.

In contrast, an electronic (e.g., digital) stethoscope may generate digital audio data via an electronic chestpiece that may include components for sound amplification, digital display, sound and other biophysical signal recording (e.g., electrocardiogram (ECG) recording), and wireless signal transmission. For example, the electronic stethoscope may wirelessly transmit audio data to a listening device (e.g., a pair of headphones or hearing aids) or a computing device (e.g., a smartphone or laptop computer) via a wireless connection, such as a Bluetooth® connection.

However, the inventors herein have recognized potential issues with digital stethoscopes. For example, many practitioners are reluctant to switch from traditional acoustic stethoscopes to digital stethoscopes due to battery life concerns. Thus, hybrid analog-digital stethoscopes have been developed that are able to function in both digital and analog (e.g., traditional acoustic) modes. Thus, when the battery is depleted, the device can still be used as a traditional acoustic stethoscope. However, mechanisms that switch between analog and digital modes demand a separate housing, for example external to the chestpiece, and thus add bulk to the stethoscope, which increases the device's volume and weight. This results in an analog stethoscope that is more cumbersome and uncomfortable for the practitioner to use.

Additionally, existing mechanisms for switching between digital and analog modes include a communication path in which acoustic sounds pass through electronic components with mechanical characteristics, such as microphones, speaker drivers, and the like, even when those electronic components are powered off. Because of the resonant frequencies of these components due to the mechanical characteristics, they can act as a damper or an amplifier in those frequencies, which adversely affects the sound that is transmitted to the wearer of the stethoscope. Consequently, while these hybrid stethoscopes offer increased sound quality in digital mode as compared to traditional acoustic stethoscopes, they also provide decreased sound quality in analog mode as compared to traditional acoustic devices.

In one example, the issues described above with hybrid analog-digital stethoscopes may be addressed by a mode switching mechanism integrated into a chestpiece of a stethoscope. The chestpiece herein disclosed includes both analog and digital components included therein for operating in either analog or digital mode. In particular, a connector of an output tube (e.g., the binaural tubing) that is configured to be inserted into the chestpiece may comprise a mode switching port. When the connector is rotated into a first, digital configuration, the connector acoustically connects the electronic components of the stethoscope to the output tube and when rotated into a second, analog configuration, the connector acoustically connects the diaphragm to the output tube. Further, when in digital mode, the connector may be acoustically isolated from the diaphragm such that only modified acoustic signals are transmitted to the wearer and when in analog mode, the connector may be acoustically isolated from the electronic components such that only unmodified acoustic signals are transmitted to the wearer.

In this way, by integrating the mode switching port into the connector, the mode switching mechanism demands no additional components, thereby mitigating any increase in bulk or size of the stethoscope. Further, when the stethoscope is in analog mode, vibrations of the diaphragm may be transmitted directly to the user without having to pass through the electronic components. Thus, the hybrid analog-digital stethoscope may provide increased sound quality in digital mode compared to a traditional stethoscope and the same sound quality in analog mode as compared to a traditional stethoscope.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

The present description relates generally to methods and systems for a digital stethoscope. In particular, methods and systems for a mode switching mechanism for a hybrid analog-digital stethoscope are herein provided. The hybrid analog-digital stethoscope herein disclosed may include a chestpiece with both analog and digital components for picking up physiological sounds (e.g., heart/lung sounds, bowel sounds, etc.) including, for example, a diaphragm (or other sound collecting interface) and a plurality of electronic components such as a microphone, an acoustic modifier, and one or more speakers. As an example, in digital mode, the microphone may capture vibration of the diaphragm and convert it to a digital signal that is processed and modified and then outputted by the one or more speakers to earpieces via a binaural tubing. In analog mode, the vibration of the diaphragm may be directly transmitted to earpieces via the binaural tubing. The mode switching mechanism may utilize a mode switching port that when rotated into a given position, puts the stethoscope in a chosen mode (e.g., analog or digital mode). The port, as will be herein described, may be a part of or otherwise integrated with a connector of the binaural tubing configured to be inserted into the chestpiece. The port is configured to form an acoustic connection (e.g., a communication path) between the binaural tubing of the stethoscope and one of a diaphragm and a speaker of the stethoscope. When the connector, and thus the port, is positioned to form an acoustic connection between the diaphragm and the binaural tubing, the stethoscope may be in an analog mode. When the connector, and thus the port, is positioned to form an acoustic connection between the speaker and the binaural tubing, the stethoscope may be in a digital mode. The port may be moved between a first position and a second position, for example by rotation or linear movement, wherein the first position corresponds to digital mode and the second position corresponds to analog mode based on movement of the chestpiece with respect to the connector.

In some examples, the mode switching port may be integrated as a portion of the connector such that rotation of a chestpiece with respect to the binaural tubing or rotation of the connector with respect to the chestpiece changes the position of the port. In this way, the mode switching mechanism may mimic how a traditional stethoscope switches between use of a bell side of a chestpiece and a diaphragm side of the chestpiece. Additionally, with the mode switching port integrated into the connector positioned in the chestpiece, the acoustic communication path formed with the port in the analog rotational position may bypass the electronic components within the chestpiece, thereby increasing sound quality when in analog mode.

Figure 1A:
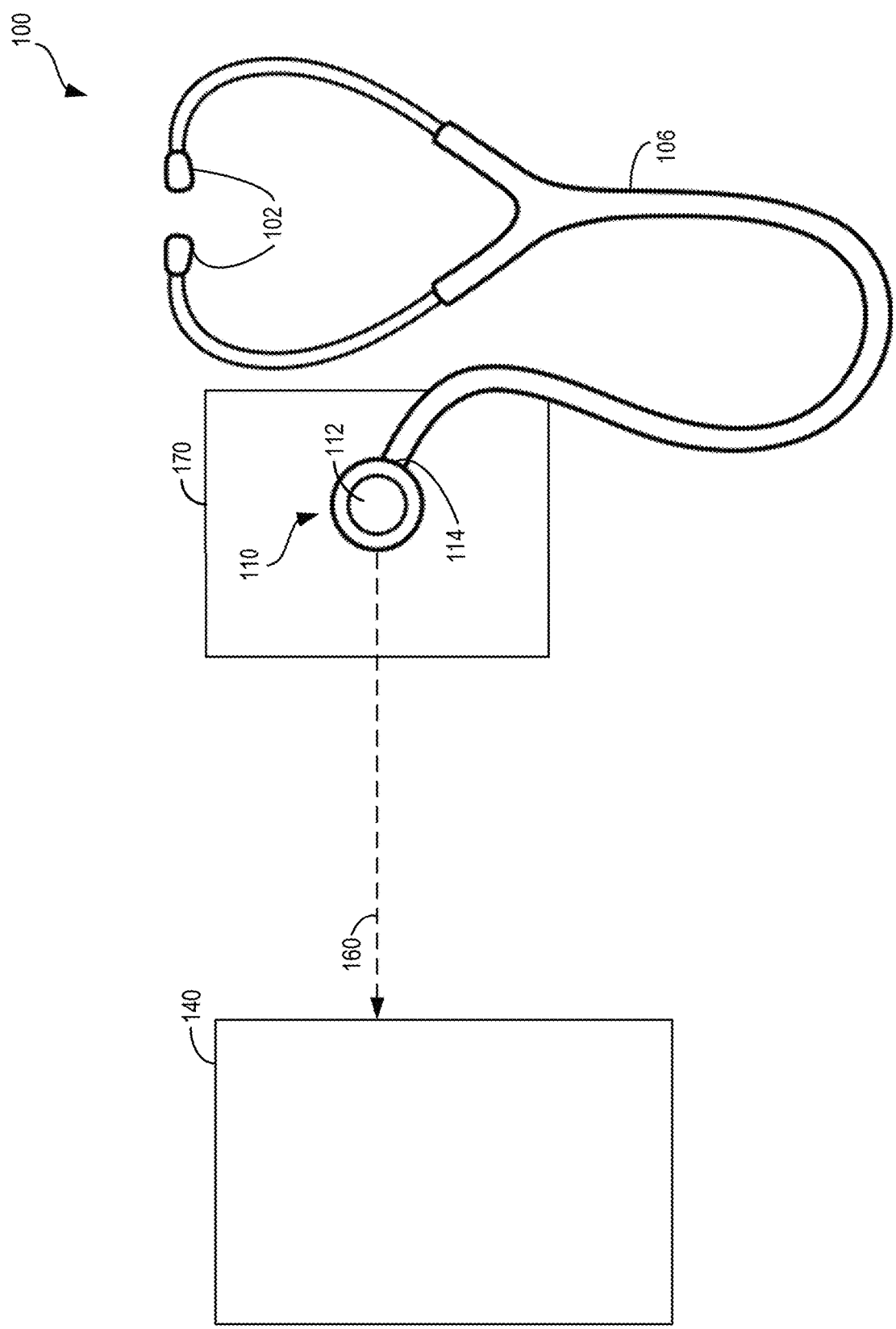
FIG. 1A is a schematic drawing showing an example digital stethoscope including earpieces connected to a chestpiece.
Figure 1B:
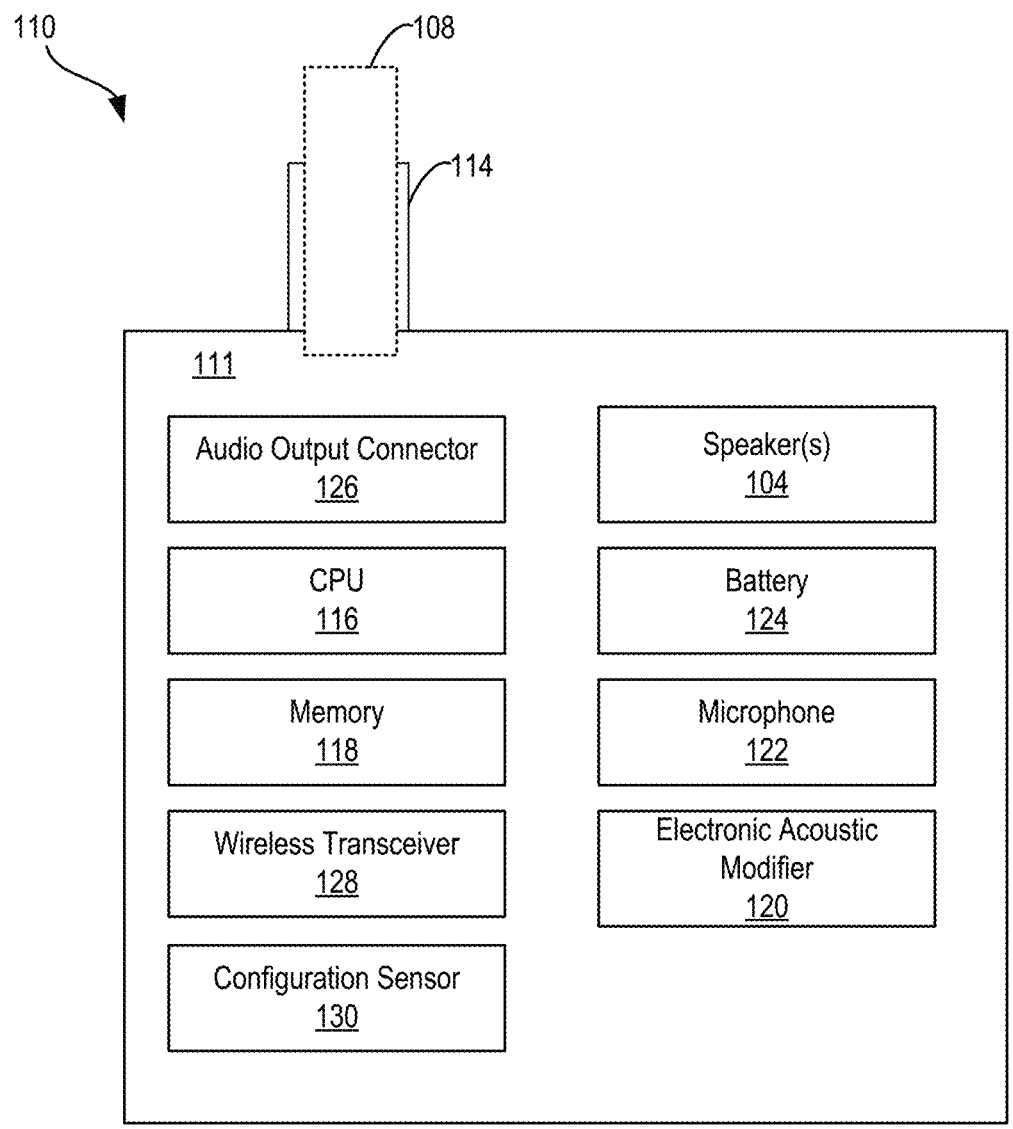
FIG. 1B is a block diagram showing the components of the chestpiece shown in FIG. 1A.

Turning now to the figures, FIGS. 1A and 1B show an electronic stethoscope 100. The electronic stethoscope 100, also referred to herein as a digital stethoscope, may be a hybrid analog-digital stethoscope that is capable of operating in both analog and digital modes. It should be appreciated that other electronic stethoscopes configured for operating in both analog and digital modes may be used without departing from the scope of this disclosure.

Referring first to FIG. 1A, the electronic stethoscope 100 includes a chestpiece 110 and an output tube 106. The chestpiece 110 is in electronic and/or acoustic communication with the output tube 106 through a connector 114 of the chestpiece. The output tube 106 includes earpieces 102 configured to be positioned in ears of a wearer to transmit recorded physiological sounds to the wearer. The output tube 106 and earpieces 102 may form a headset.

The chestpiece 110 may include a diaphragm 112, which is a sealed membrane with air inside that vibrates from external noises. The diaphragm 112 compresses or expands a volume of air inside the chestpiece 110 according to the vibrations caused by the external noises, which in turn creates sounds that may be recorded and transmitted through the connector 114 to the output tube 106. In some examples, the chestpiece 110 may include a bell in addition to the diaphragm 112. When included, the bell may be an open hollow cup or may include a smaller sealed membrane than the diaphragm 112, and air inside the bell may vibrate from external noises to produce acoustic pressure waves. The diaphragm 112 may be used for higher frequency auscultation, such as breath sounds, while the bell may be used for lower frequency auscultation, such as heart murmurs and bowel sounds. The chestpiece 110 may be placed on a patient (e.g., subject) 170 by the patient 170 or by a clinician (not shown) for auscultation. The clinician or the patient 170 may listen to bodily sounds produced by the patient through the earpieces 102.

It should be understood that the diaphragm is merely an example of a sound collecting interface that may be included in the chestpiece 110. While a diaphragm is described herein with respect to FIGS. 1A-8, other sound collecting interfaces integrated with the chestpiece 110 are possible without departing from the scope of this disclosure. For example, the sound collecting interface may be a bell or other stethoscope head configured for detecting acoustic sounds (e.g., body sounds).

In some examples, the digital stethoscope includes one or more speakers to transmit amplified audio to a user's ears, when the stethoscope is in digital mode. The one or more speakers may be positioned in the chestpiece 110, in some examples. Additional details about the one or more speakers is provided with respect to FIG. 1B.

The chestpiece 110 may connect to other electronic devices through wireless connections. For example, the chestpiece 110 may connect to an external computing device 140 via a wireless connection 160, such as a mobile device, such as a smartphone, a tablet, a smartwatch, a laptop computer, or a personal digital assistant (PDA), for example. Alternatively, the external computing device 140 may be a stationary device, such as a desktop computer or server. In still other examples, the external computing device 140 may be included in a computing network, such as a cloud computing network. The external computing device 140 may include a processor operatively connected to memory (such as random-access memory, read-only memory, flash memory, a hard disc, etc.) as well as a communications interface for sending/receiving wired or wireless signals from a network and/or other computing devices, including the chestpiece 110.

Further, in some examples, the external computing device 140 may include a user interface, such as a display for outputting information to a user and one or more of a touchscreen, a trackball, hard keys/buttons, a keyboard, a mouse, and a trackpad for receiving user inputs. The external computing device 140 may operate a software application that receives the user inputs via the user interface to adjust operation of the chestpiece. By connecting wirelessly to the external computing device 140, the chestpiece 110 may send audio data, ECG data, and/or other physiological data to the external computing device 140.

As another example, the chestpiece 110 may connect to an external listening device through another wireless connection, such as a speaker, headphones, earbuds, hearing aids, or other device capable of projecting sound and forming wireless connections to other devices. For example, sounds recorded by the chestpiece 110 may be projected by the external listening device for the patient 170 and the clinical to hear. In some examples, the external listening device may wirelessly connect to the external computing device 140 instead of the chestpiece 110. In such examples, recorded sounds may be sent from the chestpiece 110 to the external computing device 140 and from the external computing device 140 to the external listening device.

As will be elaborated below with respect to FIG. 1B, the chestpiece 110 includes components for recording and sharing auscultations. Additionally, in some examples, the chestpiece 110 may include components for recording and sharing electronic signals of a heart (e.g., electrocardiogram signals). Further, in some examples, the chestpiece 110 may be selectively disconnected from the output tube 106 and the earpieces 102 and/or rotated via the connector 114 to switch between digital mode and an analog mode.

In analog mode, as will be further herein described, auscultated acoustic sounds of the patient 170 may be transmitted through the output tube 106 without any amplification or processing, as occurs in digital mode. In digital mode, auscultated acoustic sounds of the patient 170 may be transmitted through electronic components for modification and amplification, as will be further described below.

As will be described with respect to FIGS. 3-6B, a switching mechanism may be arranged in an analog configuration or a digital configuration. When in an analog configuration, acoustic sounds auscultated from the patient 170 may be transmitted to the wearer without having to pass through the electronic components of the chestpiece 110. When in a digital configuration, acoustic sounds auscultated from the patient 170 may be transmitted to the electronic components for processing, amplification, and the like, and then transmitted to the wearer through the output tube 106.

Continuing to FIG. 1B, in some examples, the chestpiece 110 includes a body 111 that houses internal components, examples of which are elaborated below. The chestpiece 110 includes a computer processing unit (CPU) 116, such as a microcontroller unit (MCU), positioned within the body 111. The CPU 116 receives inputs and/or sends outputs to various electronic components that will be described further herein. In some examples, there is one microdevice that contains the CPU 116 and some or all of the electronic and electrical components. In some arrangements, the CPU 116 and the electronic and electrical components are positioned on two or more microdevices. The CPU 116 is operatively coupled to a memory 118, which includes one or more of a non-transitory (e.g., read-only) memory, a keep alive memory, and a random-access memory.

The chestpiece 110 may include an electronic acoustic modifier 120 in electrical communication with the CPU 116. In some examples, the electronic acoustic modifier 120 is a stand-alone device. In other examples, the electronic acoustic modifier 120 is firmware within the CPU 116. The electronic acoustic modifier 120 is configured to receive an auscultated electronic signal from one or more microphones 122 (e.g., the signal output by the one or more microphones 122, which includes vibrations of the volume of air generated by the diaphragm during auscultation), modify the auscultated electronic signal to form a modified electronic signal (e.g., amplify the electronic signal), and transmit the modified electronic signal to one or more speakers 104 configured to convert the modified electronic signal to sound output when the electronic acoustic modifier is powered on and the stethoscope is in digital mode.

The one or more speakers 104 may be positioned in the chestpiece 110, as shown. In such examples, when the stethoscope is in digital mode, the one or more speakers 104 may convert the electronic signal (e.g., received from the electronic acoustic modifier 120) to a sound output that is transmitted to a user's ears via the output tube 106 and earpieces 102.

The chestpiece 110 may include an optional audio output connector 126, such as a headphone jack or USB-type port, which can receive the modified electronic signal from the electronic acoustic modifier 120. A user may physically connect a peripheral device to the audio output connector 126. Examples of such peripheral devices include but are not limited to a computer, a cell phone, and a listening device configured to convert the modified electronic signal to sound. The audio output connector 126 may also act as a charging port in order to charge battery 124 of chestpiece 110.

In some examples, a wireless transceiver 128 is positioned in the chestpiece 110, such as within the body 111, as shown. In some examples, the wireless transceiver 128 may be included in a circuit board, such as a printed circuit board (PCB), which may also include one or more electronic components, such as the one or more microphones 122, the CPU 116, and the one or more speakers 104. The wireless transceiver 128 is in electrical communication with the electronic acoustic modifier 120. The wireless transceiver 128 is configured to receive the modified electronic signal from the electronic acoustic modifier 120, convert the modified electronic signal to a modified wireless signal, and wirelessly transmit the modified wireless signal from the chestpiece to an external listening device and/or a peripheral device, such as external computing device 140 shown in FIG. 1A. The wireless transceiver 128 may use any appropriate communication type and protocol, such as television, cellular networks, Wi-Fi, satellite, two-way radio, infrared, short-range microwave signals, IEEE 802.11 compliant radio signals, Bluetooth®, or Low Energy Bluetooth (BLE). In some examples, the wireless transceiver 128 may be configured to pair directly to the external listening device and/or the external computing device. Alternatively, the wireless transceiver 128 may communicate data to the external listening device and/or the external computing device through an intermediary device, such as a wireless router maintaining a wireless local area network (WLAN) or through a connection to the Internet. The wireless transceiver 128 may also be configured to receive signals from one or more peripheral devices, including the external computing device. In some examples, the wireless transceiver 128 is in electrical communication with the one or more microphones 122, and can wirelessly transmit the auscultated electronic signal to the external listening device and/or the external computing device without modification of the electronic signal via the electronic acoustic modifier 120. In some examples, the chestpiece 110 may include a second wireless transceiver that may thereby allow the chestpiece to establish two separate wireless connections with external devices. For example, the wireless transceiver 128 may connect to the external computing device while the second wireless transceiver connects to the external listening device.

It may be understood that sound may be projected via the speaker(s) 104 and also transmitted via the wireless transceiver 128 at the same time. For example, a user (e.g., a clinician or the patient 170) may listen to physiological sounds while placing the electronic stethoscope on the patient 170 via the earpieces 102 while one or more remote clinicians listen simultaneously via the external listening device.

In some examples, the chestpiece 110 includes a second microphone facing the external environment. The second microphone is configured to detect audio from the external environment and to convert the audio into an electronic signal. In some examples, one or both of the one or more microphones 122 and the second microphone is a micro-electrical-mechanical system (MEMS) microphone, an electret microphone, or a piezoelectric microphone. When such a second microphone is included in the chestpiece, the electronic acoustic modifier 120 is configured to receive the electronic noise signal from the second microphone and to use the electronic noise signal, for example, as part of active noise cancellation, in modifying the auscultated electronic signal to form the modified electronic signal.

In some examples, the second microphone can detect that the one or more microphones 122 is recording sounds from "open air," such as when the chestpiece 110 is held against the air, by comparing the signals coming from the two microphones. If the signals are highly correlated, the sounds that would otherwise be transmitted to the speaker(s) 104 and/or the external listening device may be suppressed. This would prevent amplification of sounds when the chestpiece 110 is not on a patient and could prevent accidental exposure to undesirable amplified sounds from such things as sirens, speech, doors closing, etc. If the two microphones detect significantly different sounds, it is an indication that the chestpiece 110 may be on a surface intended to be auscultated, and amplification could be employed.

It should be understood that, in describing electrical communication, the phrase, "A is in electrical communication with B," describes both direct electrical communication from A and B or from B and A and also electrical communication that goes between A to B through the CPU 116, (e.g., from A to the CPU 116 to B and from B to the CPU 116 to A).

Chestpiece 110 further includes the battery 124. The battery 124 may be a disposable battery or a rechargeable battery. If the battery 124 is a disposable battery, the outside of the chestpiece may include a door (not shown) through which the battery 124 may be changed/exchanged. If the battery 124 is a rechargeable battery, the outside of the chestpiece may include a charging port (as explained above) through which the battery 124 can be charged. Alternatively, the battery 124 may be charged wirelessly. The battery 124 may be configured to supply power to the electronic components of the chestpiece including, but not limited to, the one or more microphones 122, the electronic acoustic modifier 120, the second microphone (when included), the speaker(s) 104, the CPU 116, the wireless transceiver 128, and other electronic components that could be included but are not explicitly discussed herein.

Chestpiece 110 may also include one or more display outputs (not shown) positioned on an exterior of the chestpiece 110, such as indicator lights. The indicator lights and/or a display screen may provide information about the state of the electronic stethoscope 100, such as a battery state of charge, and/or provide information about the condition of the patient.

In some examples, the chestpiece 110 includes one or more devices to provide audio indicator signals (not shown) to provide sounds, such as beeps or verbal language, to indicate device operation status and/or information about the condition of the patient. In some examples, the volume of the audio indicator can be adjusted or turned off through user inputs.

In some examples, the body 111 of the chestpiece 110 may be connected to the output tube 106 shown in FIG. 1A via a connector 108 of the output tube 106 that is configured to be positioned within connector 114 of the chestpiece 110. In some examples, connector 108 and connector 114 may enable electrical connection between signal wires in the output tube 106 and the electrical components of the chestpiece 110 (e.g., the electronic acoustic modifier 120). In other examples, the connector 108 may facilitate an acoustic connection between speaker(s) 104 in the chestpiece 110 and the output tube 106 and earpieces 102. Thus, the connector 114 may house connector 108 in order to mechanically and acoustically couple the earpieces 102 to the chestpiece 110. The connector 108 may be integrated with (e.g., part of) the output tube 106 or may be a separate fitting.

In some examples, the connector 108 may be a rotatable component that allows the electronic stethoscope 100 to switch between analog mode and digital mode depending on which position the connector is in with relation to the chestpiece 110, as will be described with respect to FIGS. 5A-6B. In other examples, the connector 108 may move in a linear manner to allow for switching between analog and digital mode, as will be described with respect to FIGS. 7A-7B. One or more feedback signals may be used to determine whether or not the output tube 106/earpieces 102 are physically connected to the chestpiece 110 For example, the CPU 116 may receive feedback from a component in the earpieces 102, such as a sensor and/or the speakers 104. For example, the sensor and/or the speakers 104 in the earpieces 102 may be selectively powered when the earpieces 102 are coupled to the body 111 via the connector 114 and connector 108, whereas electronic communication between the sensors and/or the speakers 104 and the chestpiece 110 is discontinued while the earpieces 102 are disconnected from the body 111. In another example, a switch or a proximity sensor may be used to determine whether or not the earpieces 102 are connected based on detecting that the connector 108 has been inserted within connector 114 or based on a distance from the earpieces 102 from the chestpiece 110.

Further, a configuration sensor 130, switch, or other type of component within the chestpiece 110 may indicate which position the connector 108 is in, and thus in which operating mode the stethoscope is currently in. For example, the configuration sensor 130 may be configured to detect a position of the connector 108 and thus determine whether the stethoscope is in analog or digital mode. In some examples, the configuration sensor 130 may include a connecting component to connect the electronic components to the battery 124. In other examples, the connecting component may be separate from the configuration sensor 130.

Figure 2:
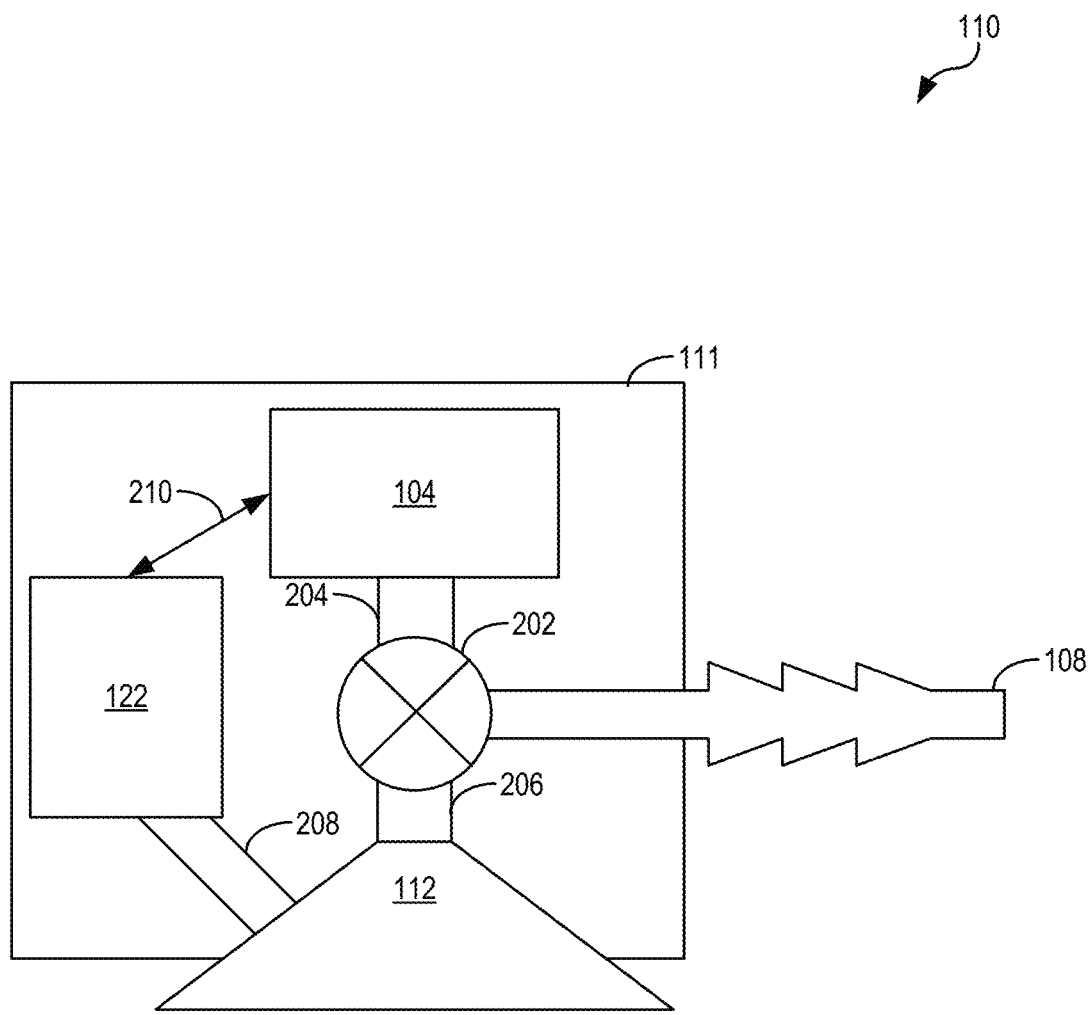
FIG. 2 is a schematic diagram of the chestpiece of FIGS. 1A and 1B including a mode switching port.

Turning now to FIG. 2, a schematic of the chestpiece 110 is shown. As described above, the chestpiece 110 includes the body 111. The one or more microphones 122 and the one or more speakers 104 may be housed within the body 111, as previously described. The connector 108 may be a component of the body 111 that may be coupled with the output tube to connect the output tube to the chestpiece 110. In some examples, the connector 108 may include or otherwise be coupled to a mode switching port 202. As will be further described below, the mode switching port 202 and connector 108 may include an acoustic channel, port, or pathway (e.g., pathway 312 shown in FIGS. 3A-3B) therewithin such that when the connector 108 is in a first position relative to the body 111 of the chestpiece 110, the pathway connects the output tube to the one or more speakers 104 and when the connector 108 is in a second position relative to the body 111, the pathway connects the output tube to the diaphragm 112.

The one or more speakers 104 may be selectively acoustically connected to the mode switching port 202 via a first acoustic channel 204. For example, when the connector 108 is in the first position for a digital configuration of the stethoscope, the first acoustic channel 204 may be in acoustic communication with the pathway of the mode switching port 202. The diaphragm 112 may be selectively acoustically connected to the mode switching port 202 via a second acoustic channel 206. For example, when the connector 108 is in the second position for an analog configuration of the stethoscope, the second acoustic channel 206 may be in acoustic communication with the mode switching port 202.

In some examples, when the connector 108 is in the first position for digital mode, the mode switching port 202 and/or connector 108 may form an air tight seal with the second acoustic channel 206, or otherwise acoustically isolate from the second acoustic channel 206, such that any unmodified acoustic signals may not be transmitted to the output tube directly from the diaphragm 112. Further, when the connector 108 is in the second position for analog mode, the mode switching port 202 and/or the connector 108 may form an air tight seal with the first acoustic channel 204, or otherwise acoustically isolate from the second acoustic channel 206, such that any signals unmodified acoustic signals transmitted from the diaphragm 112 are not modified by the mechanical characteristics of the one or more speakers 104 and/or the one or more microphones 122.

The diaphragm 112 may additionally be acoustically connected to the one or more microphones 122 via a third acoustic channel 208. The third acoustic channel 208 may be a separate pathway from the first and second acoustic channels 204, 206 that connect to the mode switching port 202. Auscultated sounds acquired by the diaphragm 112 may be transmitted to the one or more microphones 122 via the third acoustic channel 208. As described with respect to FIG. 1B, the one or more microphones 122 may be in electronic communication with the one or more speakers 104 via an electronic connection 210. For example, both the one or more microphones 122 and the one or more speakers 104 may be included in a PCB. In another example, the one or more microphones 122 may be positioned within the cavity of the diaphragm or other sound collecting interface and may be connective to the one or more speakers and other electronic components via a separate electronic connection. In such examples, the third acoustic channel 208 may be omitted.

While the one or more speakers 104 are shown herein positioned 180 degrees opposite the diaphragm 112, it should be understood that other configurations may be possible without departing from the scope of this disclosure. For example, the one or more speakers 104 may be angled with respect to the diaphragm 112 and the pathway of the mode switching port 202 may be configured to switch between connecting to the diaphragm and connecting to the one or more speakers 104 in their given configurations.

In some examples, the position of the connector 108 and thus the configuration of the mode switching port 202 may turn off and on the electronic components within the body 111. For example, when the connector 108 is in the first position and the mode switching port 202 is in acoustic communication with the one or more speakers 104 via the first acoustic channel 204, a switch, sensor, or other device may be activated so as to power on the electronic components, including the one or more microphones 122 and the one or more speakers 104. Further, when the mode switching port 202 is in the analog configuration when the connector 108 is in the second position, the switch, sensor, or other device may be deactivated so as to power off the electronic components. Thus, when the electronic stethoscope 100 is in analog mode, the electronic components may be powered off, which may serve to preserve battery charge.

Figure 3A:
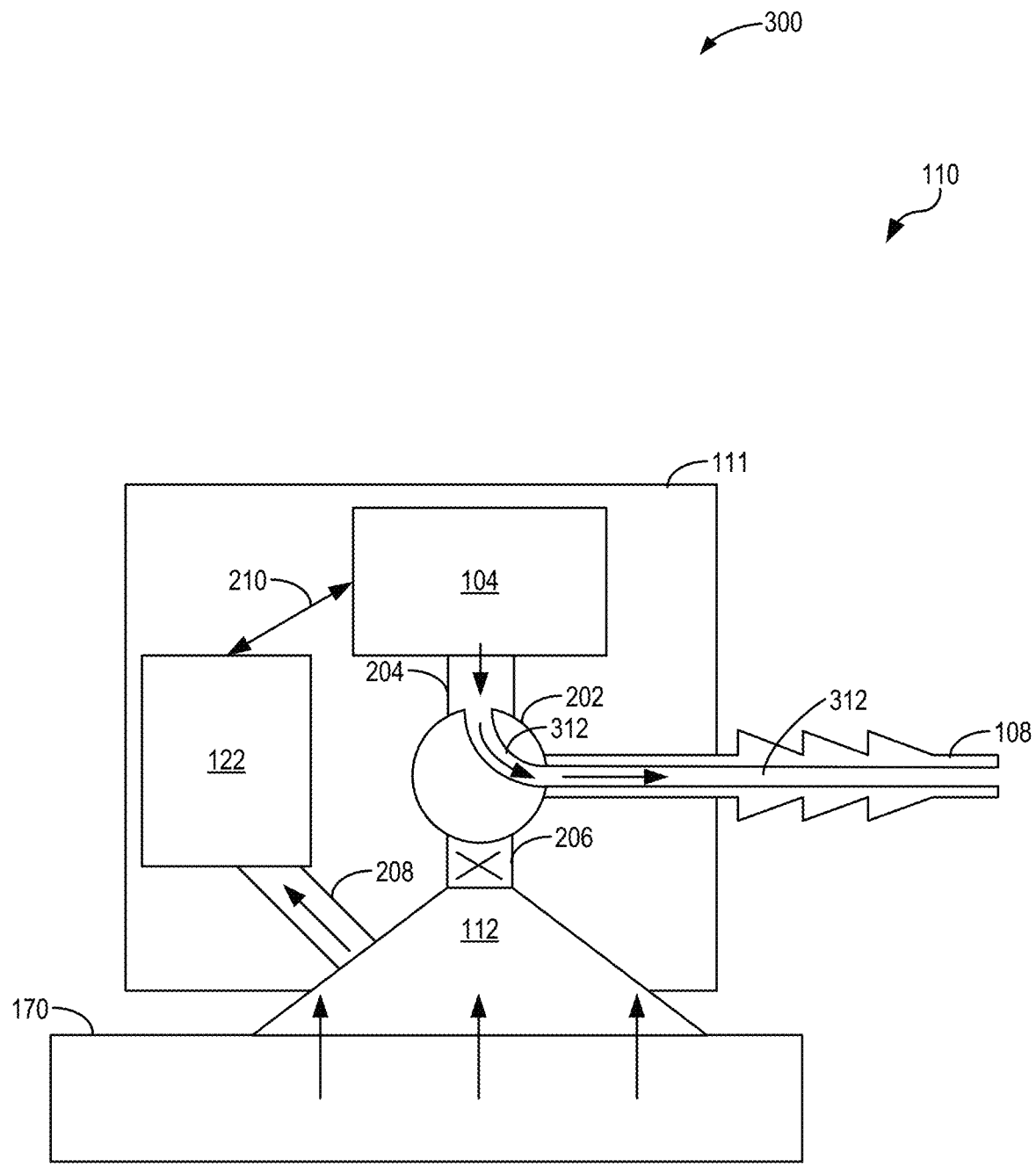
FIG. 3A is a schematic diagram of the chestpiece with the mode switching port in a first configuration.

Referring now to FIG. 3A, a first configuration 300 of the chestpiece 110 is shown. The first configuration 300 may be a digital configuration. In the first configuration 300, the connector 108 and the mode switching port 202 may be in the first position. As noted, the connector 108 and the chestpiece 110 may be moveable with respect to one another, for example via rotation about an axis, linear translation, or another type of relative movement.

In examples where movement is accomplished via relative rotation, the connector 108 may rotate within the body 111 of the chestpiece 110 when the connector 108 is connected to the chestpiece 110. In other examples, the chestpiece 110 may rotate about the connector 108. Rotation may be performed by the wearer manually when a change in operation mode is desired. The connector 108 and the chestpiece 110 may be unfixed components such that rotation of either alters the relative rotational arrangement.

In examples where movement is accomplished linearly, the connector 108 and the chestpiece 110 may move linearly with respect to one another. In some examples, the connector 108 may move linearly within a stationary chestpiece 110. In other examples, the chestpiece 110 may move linearly about a stationary connector 108. The connector 108 and the chestpiece 110 may be unfixed components such that linear movement of either alters the relative linear arrangement.

When the electronic stethoscope is in the first configuration 300, acoustic sounds of a patient, such as patient 170 described with respect to FIG. 1A, may be detected by the diaphragm 112. Vibrations of the volume of air generated by the diaphragm 112 during auscultation may be transmitted to the one or more microphones 122 via the third acoustic channel 208. The one or more microphones 122 may capture the vibrations generated by the diaphragm 112 and may produce an electronic signal. The electronic signal may be transmitted to the one or more speakers 104 via the electronic connection 210. As described above, the electronic signal may be amplified, modified, and/or otherwise processed on its way to the one or more speakers 104, for example by the electronic acoustic modifier 120 described with respect to FIG. 1B.

The one or more speakers 104 may output modified acoustic signals to the wearer of the electronic stethoscope. For example, the one or more speakers 104 may output the modified acoustic signals to the output tube via the connector 108 when the mode switching port 202 is in the first position in which a pathway 312 thereof forms an acoustic connection between the first acoustic channel 204 and the output tube, which, as described with respect to FIG. 1B, is fluidly connected to the connector 108. The pathway 312 may be an acoustic channel that is formed as a cavity within the connector 108.

As noted, when the mode switching port 202 is in the first position, the mode switching port 202 may form an air tight seal with the second acoustic channel 206, or otherwise acoustically isolate the second acoustic channel 206 from the one or more speakers 104. Thus, the vibrations of the diaphragm 112 may not be transmitted to the user without undergoing modification by the electronic components. In this way, in digital mode, only the modified acoustic signals may be transmitted to the wearer.

Figure 3B:
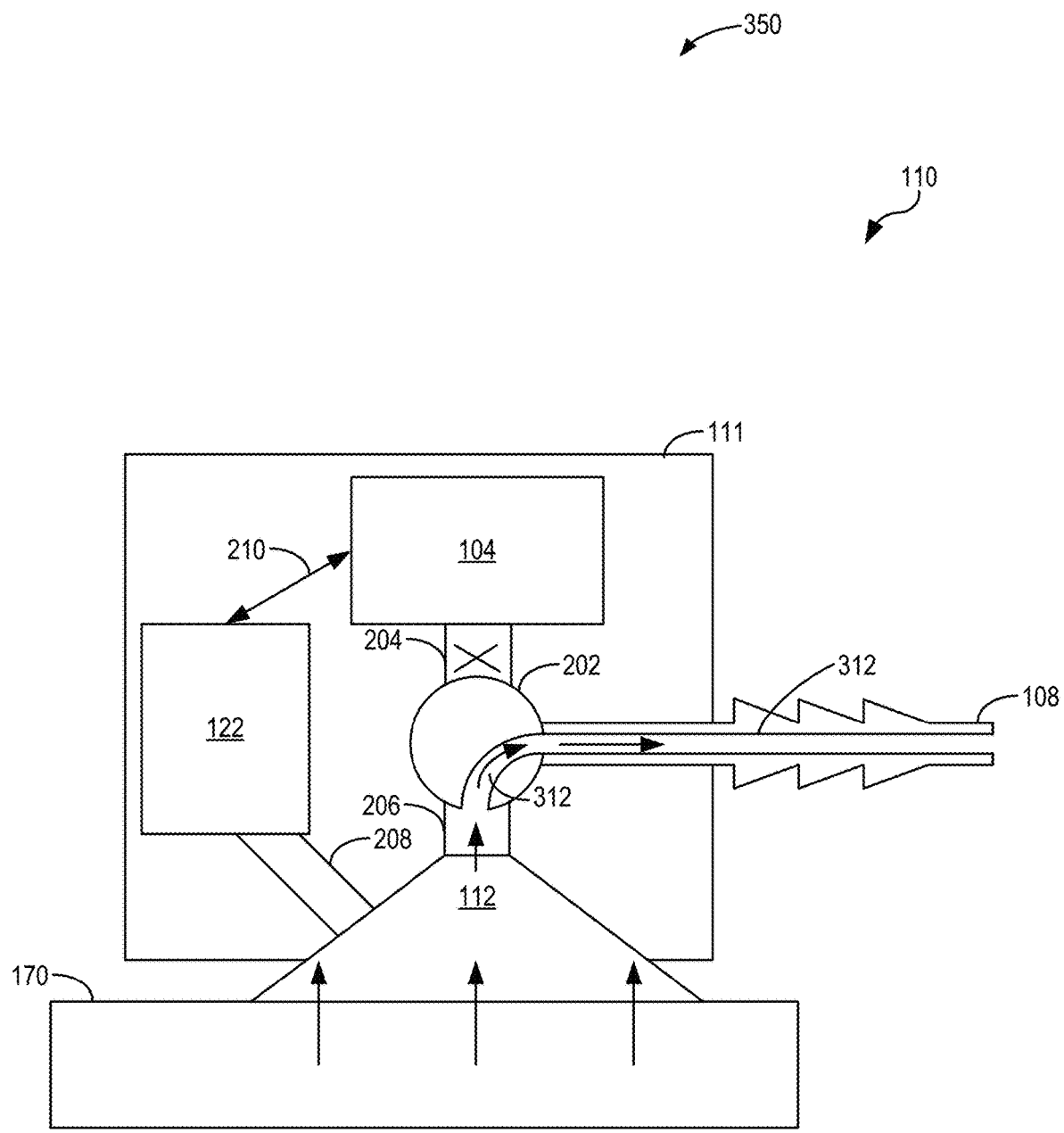
FIG. 3B is a schematic diagram of the chestpiece with the mode switching port in a second configuration.

In contrast, in analog mode, only unmodified acoustic sounds may be transmitted to the wearer. FIG. 3B shows the chestpiece 110 in a second configuration 350, which may be an analog configuration. In the second configuration 350, the connector 108 and the mode switching port 202 may be in the second position. As an example when mode switching is accomplished via rotation, to transition the electronic stethoscope 100 from the first configuration 300 to the second configuration 350, the connector 108 may be rotated counterclockwise with respect to the chestpiece 110 and to transition the electronic stethoscope from the second configuration 350 to the first configuration 300, the connector 108 may be rotated clockwise with respect to the chestpiece 110. In other examples, such as when the diaphragm 112 and the one or more speakers 104 are positioned 180 degrees opposite each other, the connector 108 may be switched between the first and second configurations via rotation in either direction.

When the electronic stethoscope is in the second configuration 350, acoustic sounds of a patient, such as patient 170 described with respect to FIG. 1A, may be detected by the diaphragm 112. Vibrations of the volume of air generated by the diaphragm 112 during auscultation may be transmitted through the second acoustic channel 206. The unmodified acoustic signals detected by the diaphragm 112 may then be transmitted to the wearer of the electronic stethoscope. For example, diaphragm 112 may output the unmodified acoustic signals to the output tube via the connector 108 when the mode switching port 202 is in the second position in which the pathway 312 thereof forms an acoustic connection between the second acoustic channel 206 and the output tube.

As noted, when the mode switching port 202 is in the second position, the mode switching port 202 may form an air tight seal with the first acoustic channel 204, or otherwise acoustically isolate the first acoustic channel 204 from the second acoustic channel 206. Thus, the vibrations of the diaphragm 112 may not be modified by the mechanical characteristics of the electronic components (e.g., the one or more microphones 122, the one or more speakers, the electronic acoustic modifier 120, and/or the like) on their way to the output tube. Any signals that are transmitted through the third acoustic channel 208 rather than into the second acoustic channel 206 may not enter the pathway 312 of the connector 108 due to acoustic isolation between the first acoustic channel 204 and the mode switching port 202.

In this way, by incorporating the mode switching port with the connector as a moveabe component, auscultated sounds may be transmitted to the wearer in analog mode without any degradation that would result from passing through electronic components. Thus, in analog mode, the hybrid analog-digital stethoscope may function with the same sound quality as a traditional acoustic stethoscope. Further, with the mode switching port incorporated into the connector, which is an existing component in hybrid analog-digital stethoscope devices, any increase in bulk, complexity, and weight of the device that would result from adding a separately housed or additional mode switching mechanism or device may be mitigated.

Figure 4:
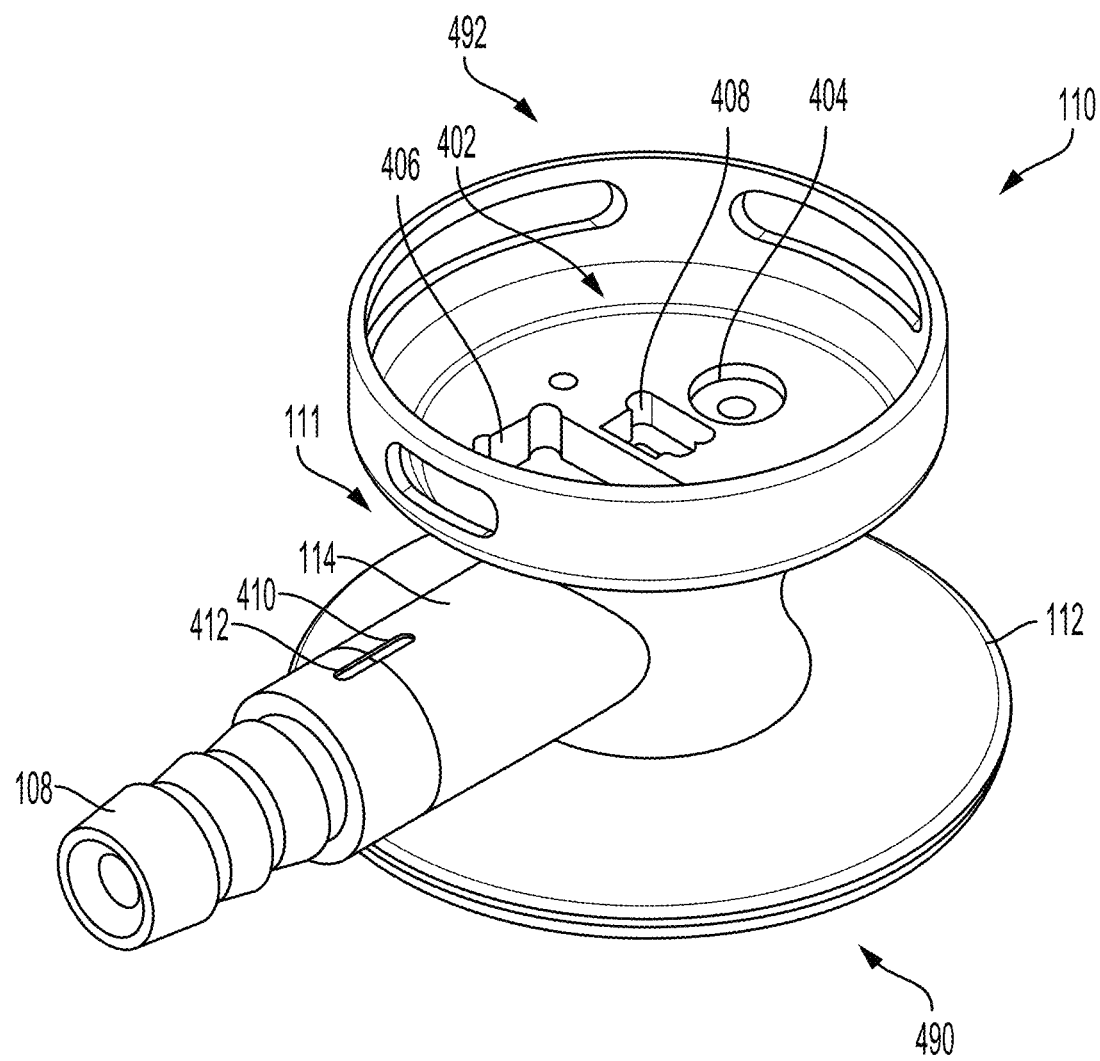
FIG. 4 is a detailed perspective view of the chestpiece of FIG. 2.
Figure 5A:
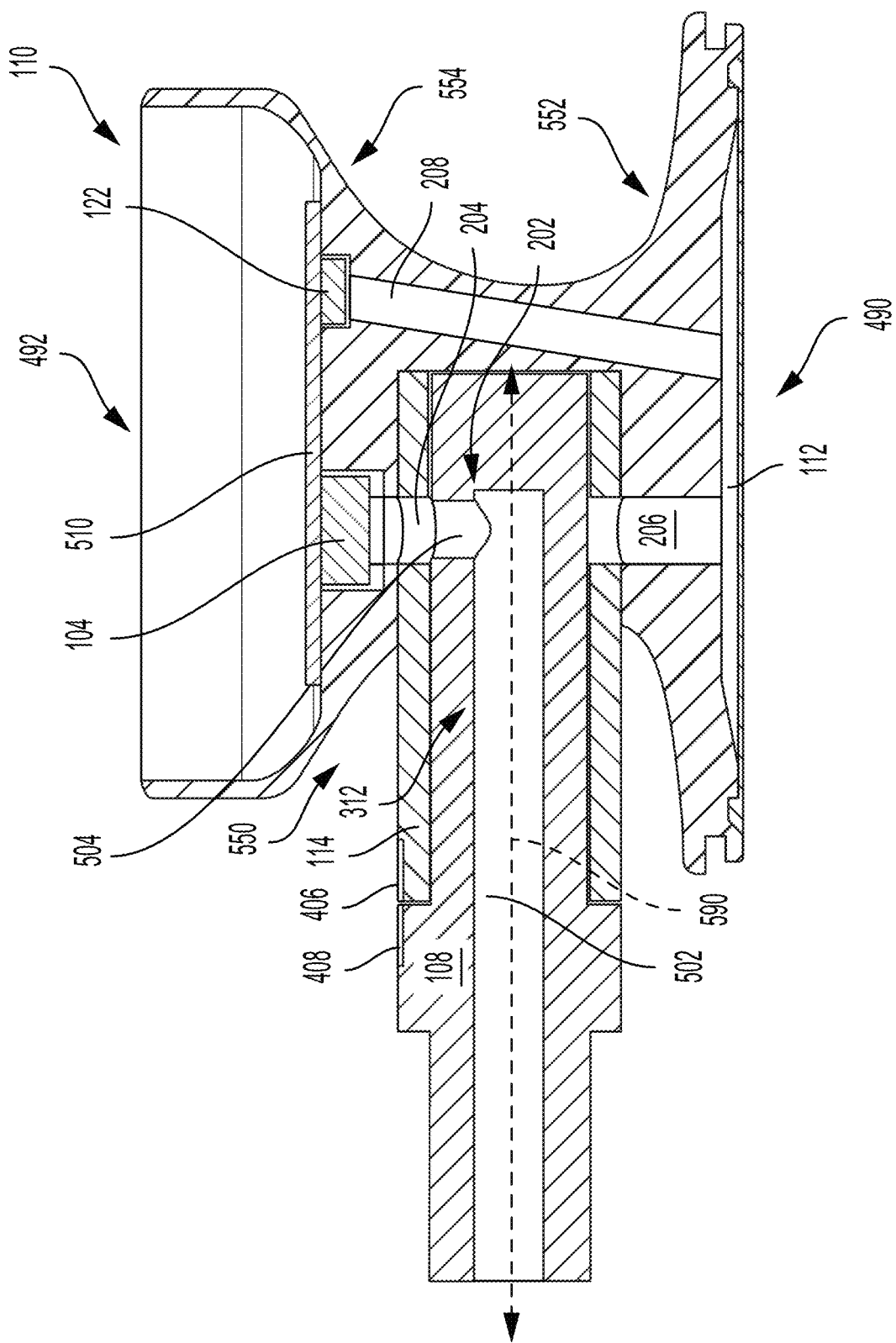
FIG. 5A is first cross-sectional view of the chestpiece in analog mode according to a first example.
Figure 5B:
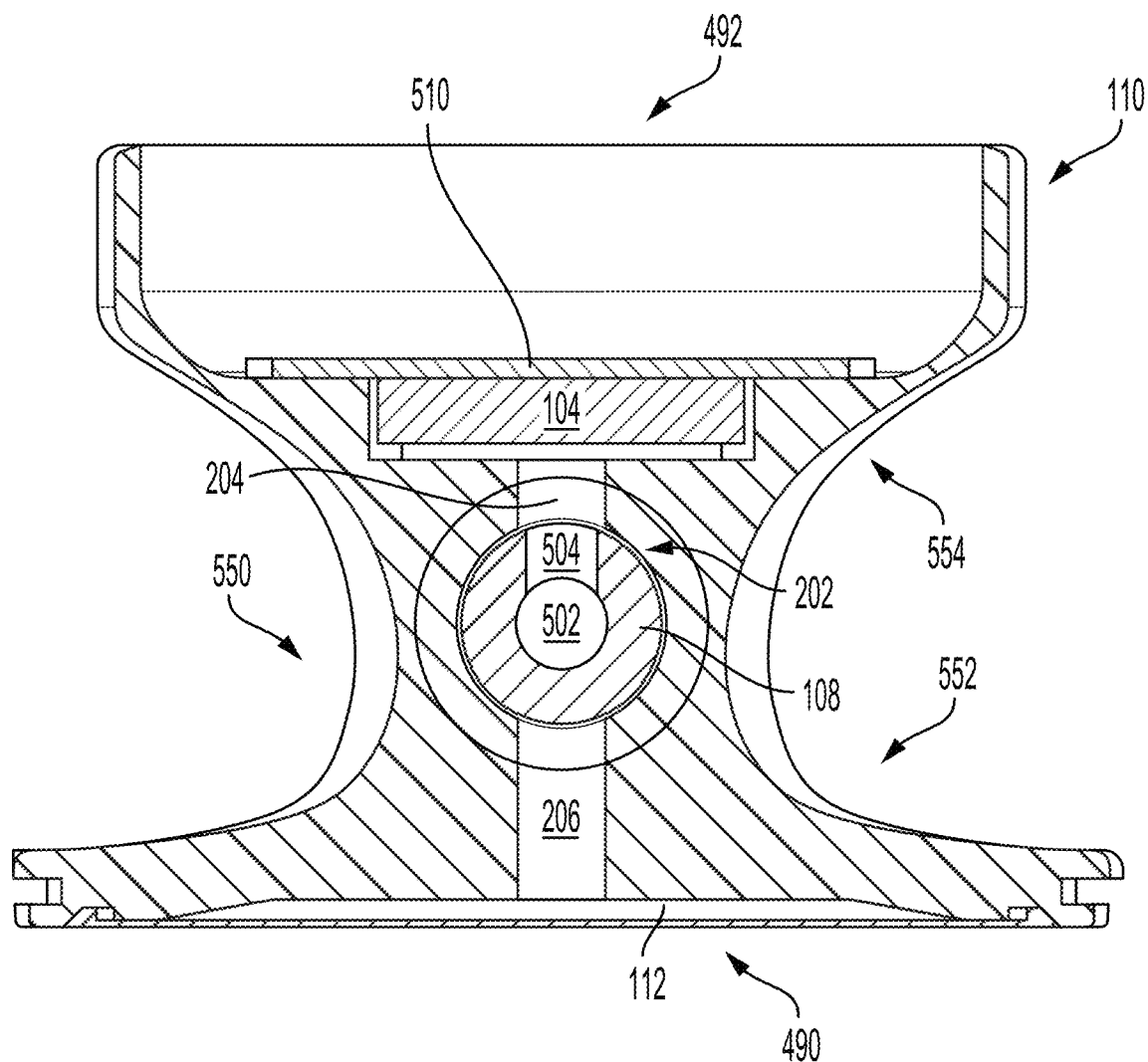
FIG. 5B is a second cross-sectional view of the chestpiece in analog mode according to the first example.
Figure 6A:
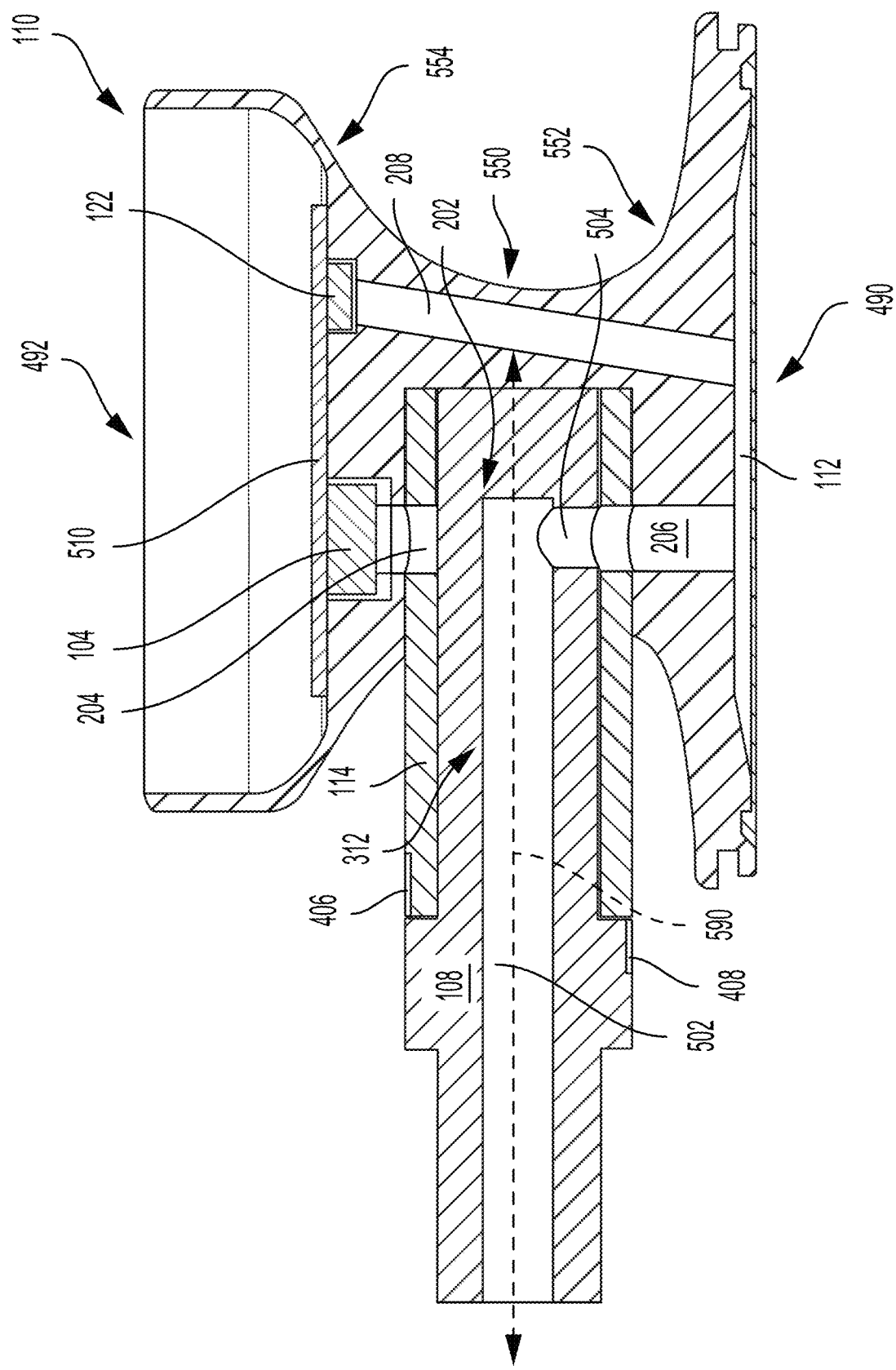
FIG. 6A is a first cross-sectional view of the chestpiece in digital mode according to the first example.
Figure 6B:
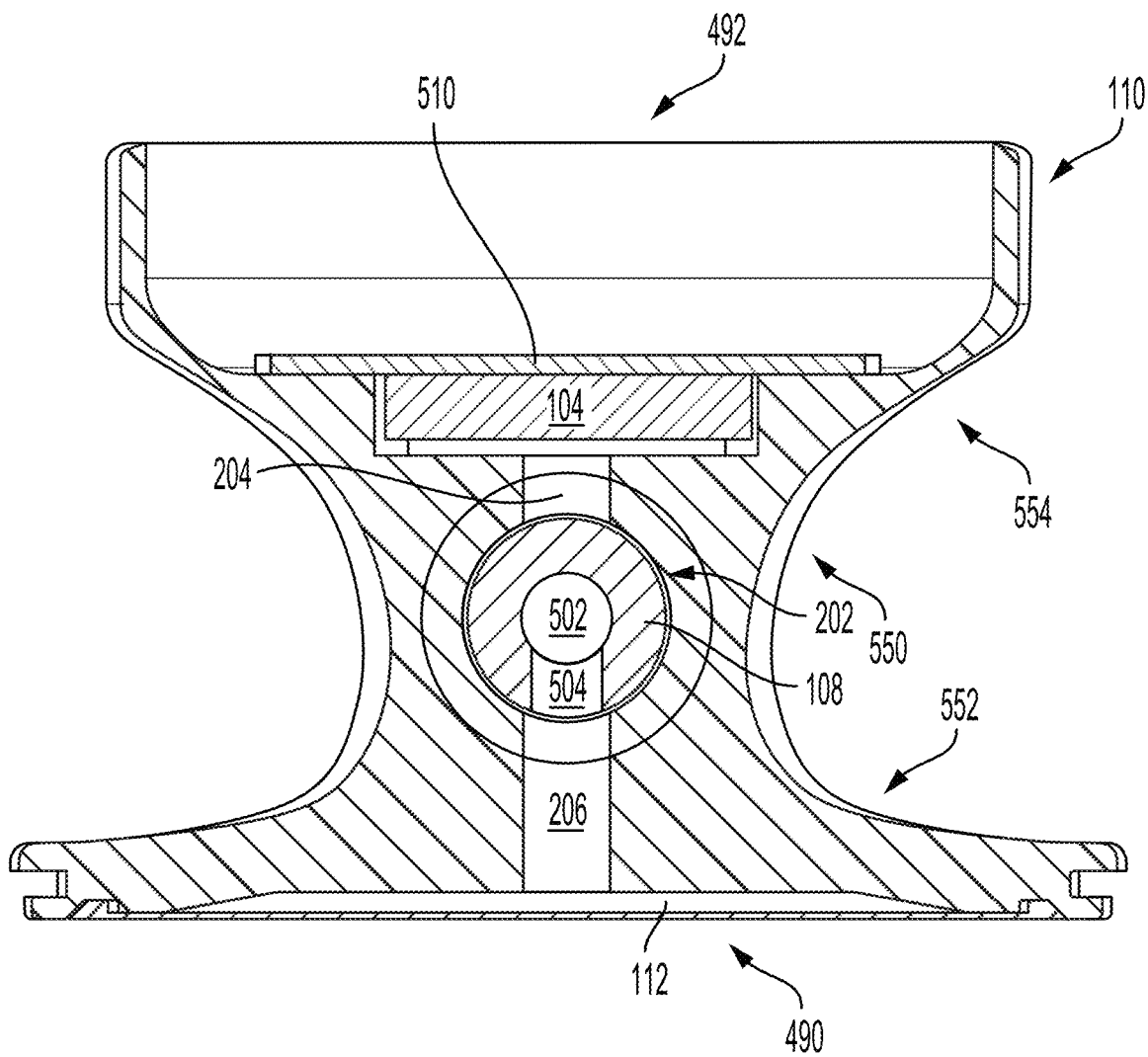
FIG. 6B is a second cross-sectional view of the chestpiece in digital mode according to the first example.

Turning to FIGS. 4-6B, a detailed example of the chestpiece 110 is shown. In particular, the chestpiece 110 is shown in FIG. 4 in a perspective view. Cross-sectional views of the chestpiece 110 when in the first, digital configuration are shown in FIGS. 5A and 5B and cross-sectional views of the chestpiece 110 when in the second, analog configuration are shown in FIGS. 6A and 6B when the mode switching mechanism involves rotation of the connector 108 with respect to the chestpiece 110.

The chestpiece 110 includes the diaphragm 112 and a plurality of electronic components, as herein described. The electronic components comprise the one or more microphones 122 and the one or more speakers 104. In some examples, the one or more microphones 122, the one or more speakers 104, and/or other electronic components may be integrated into a PCB (e.g., PCB 510 shown in FIGS. 5A-6B). For example, the PCB may be positioned atop a surface 402 of the chestpiece 110. The surface 402 may include a microphone housing 404 and a speaker housing 406. When the PCB is positioned atop of the surface 402, the one or more microphones 122 may reside within the microphone housing 404 and the one or more speakers 104 may reside within the speaker housing 406. In the example shown in FIG. 4, the diaphragm 112 is positioned towards a first end 490 and the PCB with the electronic components are positioned towards a second end 492, where the first end 490 is 180 degrees opposite the second end 492.

As described with respect to FIG. 1B, the chestpiece 110 may include the connector 114 portion of the body 111. The connector 108 may be incorporated as a component of the body 111 of the chestpiece 110, wherein the connector 108 is nested within the connector 114, and may be configured to couple to the output tube of the stethoscope. In the example of the chestpiece 110 depicted in FIG. 4, the connector 114 includes a first alignment divot 410 and the connector 108 includes a corresponding second alignment divot 412. The first and second alignment divots 410, 412 may be positioned toward the second end 492. In some examples, a third alignment divot may also be included in the connector 108 toward the first end 490 and/or a fourth alignment divot may also be included in the connector 114 toward the first end 490. The alignment divots as herein described may allow a user to determine whether the connector 108 and chestpiece 110 are properly aligned in one of the first and second configurations. For example, when the first and second alignment divots 410, 412 are aligned, the stethoscope may be in digital mode wherein the pathway (e.g., pathway 312 shown in FIGS. 3A-3B) is in acoustic communication with the one or more speakers 104 and forms an air tight seal or other acoustic isolation with the diaphragm 112. When the first and second alignment divots 410, 412 are not aligned, the stethoscope may be in analog mode, wherein pathway may be in acoustic communication with the diaphragm and forms an air tight seal or other acoustic isolation with the one or more speakers 104.

In some examples, the chestpiece 110 may also comprise a sensor housing 408 configured to house the sensor (e.g., the configuration sensor 130) that is configured to determine a current configuration of the chestpiece 110 (e.g., analog configuration or digital configuration). The configuration sensor 130 may be a switch, a pressure sensor, a magnet sensor, a Hall effect sensor, or any other suitable sensor. In some examples, for particular types of sensors, the connector 108 may include components, like small protrusions for switches or pressure sensors, magnets for magnet sensors, or the like, that may be detected by the sensor in order to determine which configuration the device is in based on the position of the connector. In some examples, the sensor may be incorporated into the PCB along with the other electronic components.

In the digital configuration, as shown in FIGS. 5A and 5B, the connector 108 may be positioned within the connector 114 in the first position. The pathway 312 of the connector 108 and the mode switching port 202 may comprise a first section 502 and a second section 504. In some examples, the first section 502 may be the portion of the pathway 312 that is within the body of the connector 108 and the second section 504 is the mode switching port 202. In some examples, the first and second sections 502, 504 may be formed as part of the same channel within the connector 108. In other examples, the connector 108 with the first section 502 may be formed separate from the second section 504 and assembled during manufacture.

The first section 502 may be parallel with an axis of rotation 590 of the connector 108. The second section 504 may be perpendicular to the axis of rotation 590. Thus, as the connector 108 rotates about its axis of rotation 590, the position of the second section 504 relative to the first and second ends 490, 492 changes. Thus, by rotating the connector 108 with respect to the chestpiece 110, the electronic stethoscope may be put in the digital configuration as shown in FIGS. 5A and 5B by positioning the second section 504 towards the second end 492.

It should be understood that the axis of rotation 590 is described herein with respect to the connector 108, the axis of rotation and the relative rotation of the second section of the pathway may also apply to the chestpiece in examples in which the chestpiece rotates about the connector 108.

The connector 108 is configured to nest within the connector 114 of the chestpiece 110 when the chestpiece 110 is assembled. The connector 114 of the chestpiece 110 may extend from a middle section 550. The middle section 550 may connect to a first end section 552 in which the diaphragm 112 is positioned and to a second end section 554 in which the PCB 510 is positioned.

The chestpiece 110 may take on an hourglass shape, in some examples, in which from the first end section 552, the chestpiece 110 narrows towards the middle section 550 and then broadens from the middle section 550 towards the second end section 554. This hourglass shape may facilitate gripping by the wearer, making it easier for the wearer to hold the chestpiece 110 and rotate it to switch between modes.

In the analog configuration, as shown in FIGS. 6A and 6B, the connector 108 may be positioned within the connector 114 with the mode switching port 202 in the second position. Compared to the digital configuration, in the analog configuration, the second section 504 may be positioned towards the first end 490 so as to form an acoustic connection with the second acoustic channel 206. In the example shown in FIGS. 4-6B, to transition between the digital configuration and the analog configuration, the connector 108 may be rotated relative to the chestpiece 110.

Figure 7A:
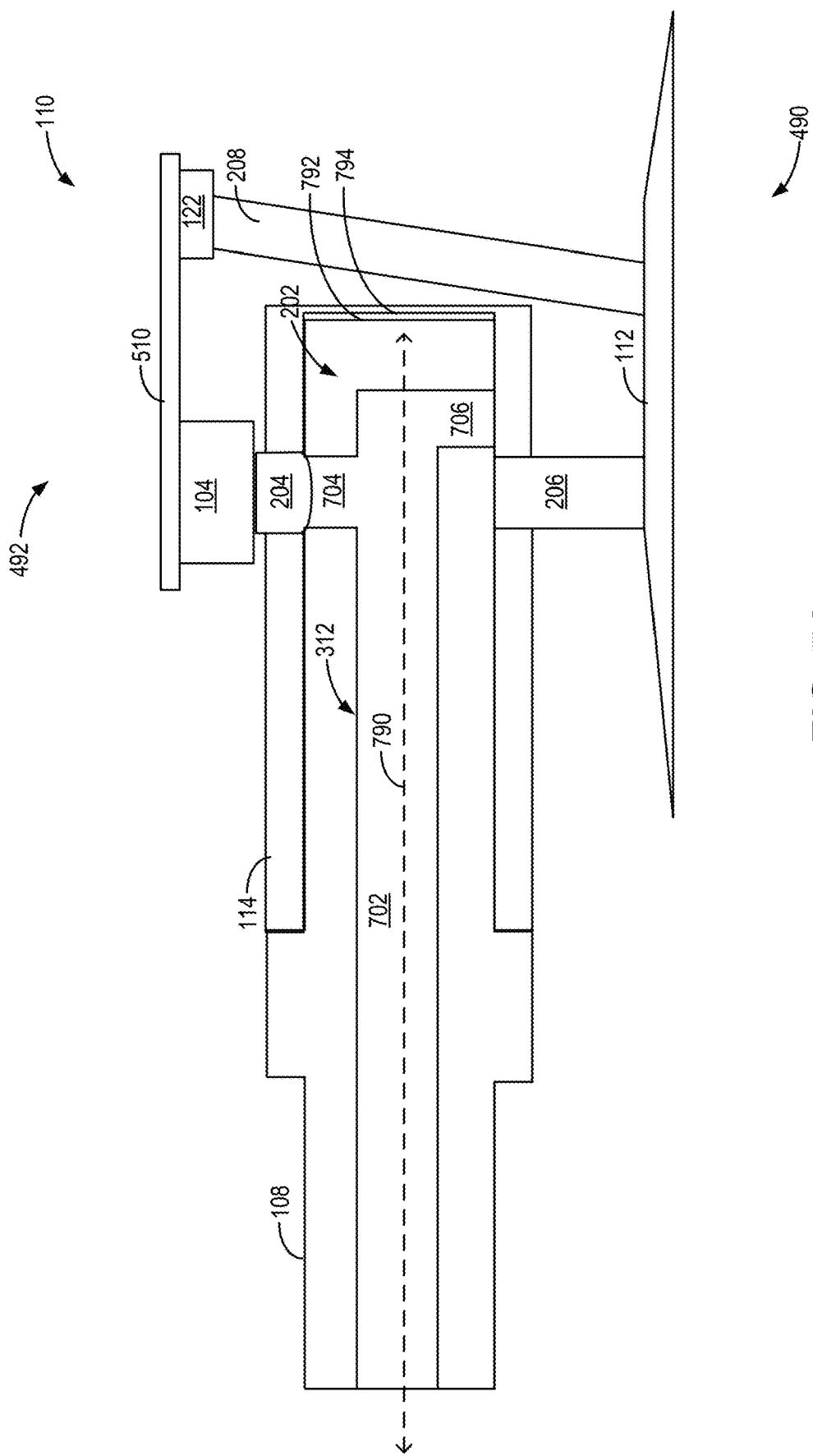
FIG. 7A is a schematic view of the chestpiece in digital mode, according to a second example.
Figure 7B:
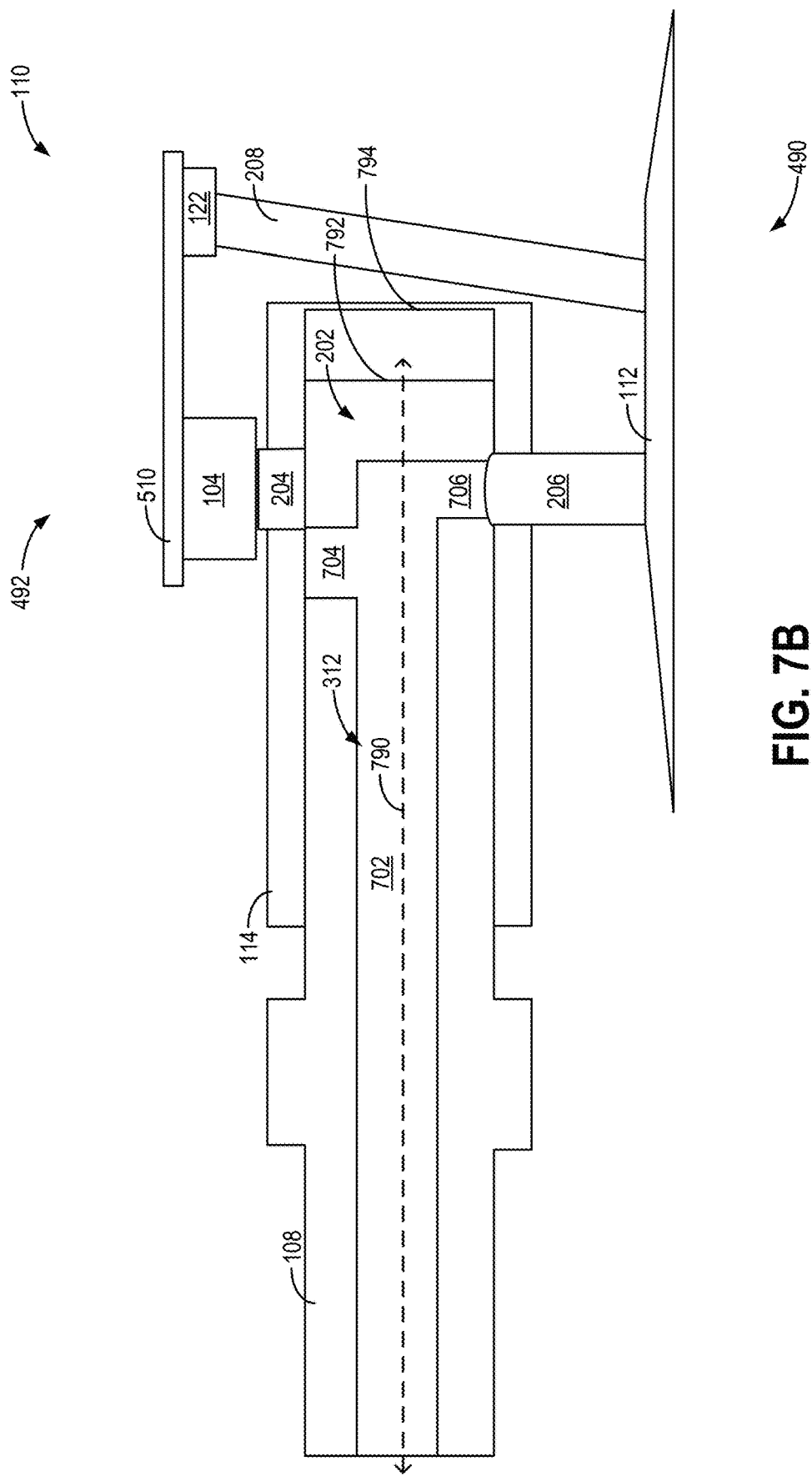
FIG. 7B is a schematic view of the chestpiece in analog mode, according to the second example.

Turning now to FIGS. 7A and 7B, a schematic view of the chestpiece 110 is shown. FIG. 7A shows the chestpiece 110 in a first, digital configuration and FIG. 7B shows the chestpiece 110 in a second, analog configuration. As opposed to FIGS. 5A-6B, in FIGS. 7A-7B, movement of the connector 108 with respect to the chestpiece 110 to switch between the digital and analog modes may be a linear motion.

For example, the pathway 312 within the connector 108 may include a first section 702, a second section 704, and a third section 706. The first section 702 may be the portion of the pathway 312 that is within the body of the connector 108, similar to the first section 502 described above. The second and third sections 704, 706 may be the mode switching port 202. The second and third sections 704, 706 may branch in different directions from the first section 702. For example, the second section 704 may branch off the first section 702 towards the second end 492 and the third section 706 may branch off the first section 702 towards the first end 490. It should be understood however that the second and third sections may branch in other directions based on the particular positions of the acoustic channels within the chestpiece 110.

In FIG. 7A, the connector 108 is shown in a first position with respect to the chestpiece 110 (e.g., with respect to the connector 114) along an axis of linear movement 790. In the first position, the second section 704 of the pathway 312 may be in acoustic communication with the first acoustic channel 204 so as to acoustically connect the output tube with the one or more speakers 104 via the pathway 312. At the same time, in the first position, the third section 706 may be acoustically isolated from the second acoustic channel 206.

In FIG. 7B, the connector 108 is shown in a second position with respect to the chestpiece 110 (e.g., with respect to the connector 114) along the axis of linear movement 790. In the second position, the third section 706 of the pathway 312 may be in acoustic communication with the second acoustic channel 206 so as to acoustically connect the output tube with the diaphragm 112 via the pathway 312. At the same time, in the second position, the second section 704 may be acoustically isolated from the first acoustic channel 204.

To transition the stethoscope from digital to analog mode when mode switching is accomplished via linear movement, the connector 108 may be linearly translated along the axis of linear movement 790 with respect to the chestpiece 110 (e.g., with respect to the connector 114). For example, the connector 108 may be pulled linearly out of the connector 114 in order to switch from the first position to the second position and may be pushed linearly into the connector 114 in order to switch from the second position to the first position.

Further, with the connector 108 in the first position, the electronic components, including the one or more microphones 122 and the one or more speakers 104 may be powered on. For example, a switch may be positioned between a first surface 792 of the connector 108 and a second surface 794 of the connector 114, wherein the first surface 792 of the connector 108 is in closer proximity to the second surface 794 of the connector 114 when the connector 108 is in the first position compared to when the connector 108 is in the second position. Thus, when the connector 108 is in the second position, the switch may be toggled off and when the connector 108 is in the first position, the switch may be toggled on.

As previously described with respect to FIG. 3A, in the digital configuration shown in FIGS. 5A-5B and 7A, auscultated sounds may be detected by the diaphragm 112, converted to electronic signals by the one or more microphones 122, amplified or otherwise modified, and then outputted to the wearer via the output tube. The modified acoustic signals may be outputted by the one or more speakers 104 into the first acoustic channel 204, which, in the digital configuration, is in acoustic communication with the pathway 312 (e.g., via the second section 504 as described with respect to FIGS. 5A-5B or the second section 704 as described with respect to FIG. 7A). Thus, modified signals may enter the pathway 312 and be outputted to the wearer via the output tube. Further, due to the acoustic isolation between the connector 108 and the second acoustic channel 206, no unmodified auscultated signals may reach the wearer in digital mode.

As previously described with respect to FIG. 3B, in the analog configuration shown in FIGS. 6A-6B and 7B, auscultated sounds may be detected by the diaphragm 112 and outputted directly to the output tube. For example, sounds detected by the diaphragm 112 may be outputted to the second acoustic channel 206, which is in acoustic communication with the pathway 312 (e.g., via the second section 504 as described with respect to FIGS. 6A-6B or via the third section 706 as described with respect to FIG. 7B). Thus, unmodified signals may enter the pathway 312 and be outputted to the wearer via the output tube. Further, due to the acoustic isolation between the connector 108 and the first acoustic channel 204, in analog mode, the auscultated sounds may be modified by the mechanical characteristics of the electronic components. Thus, the wearer may receive auscultated sounds from the patient without any degradation that would result from the signals passing through powered-off electronic components.

Additionally, forming the mode switching port 202 as part of the connector 108, with the pathway 312 being formed therewithin with two or more sections, the demand for additional components to allow for switching between digital and analog mode may be reduced. Further, in some examples, such as when switching between modes is accomplished via relative rotation, the mechanism of switching between analog and digital mode may mimic the mechanism of switching between usage of a bell and a diaphragm in a traditional stethoscope and may therefore be more intuitive for practitioners.

Figure 8:
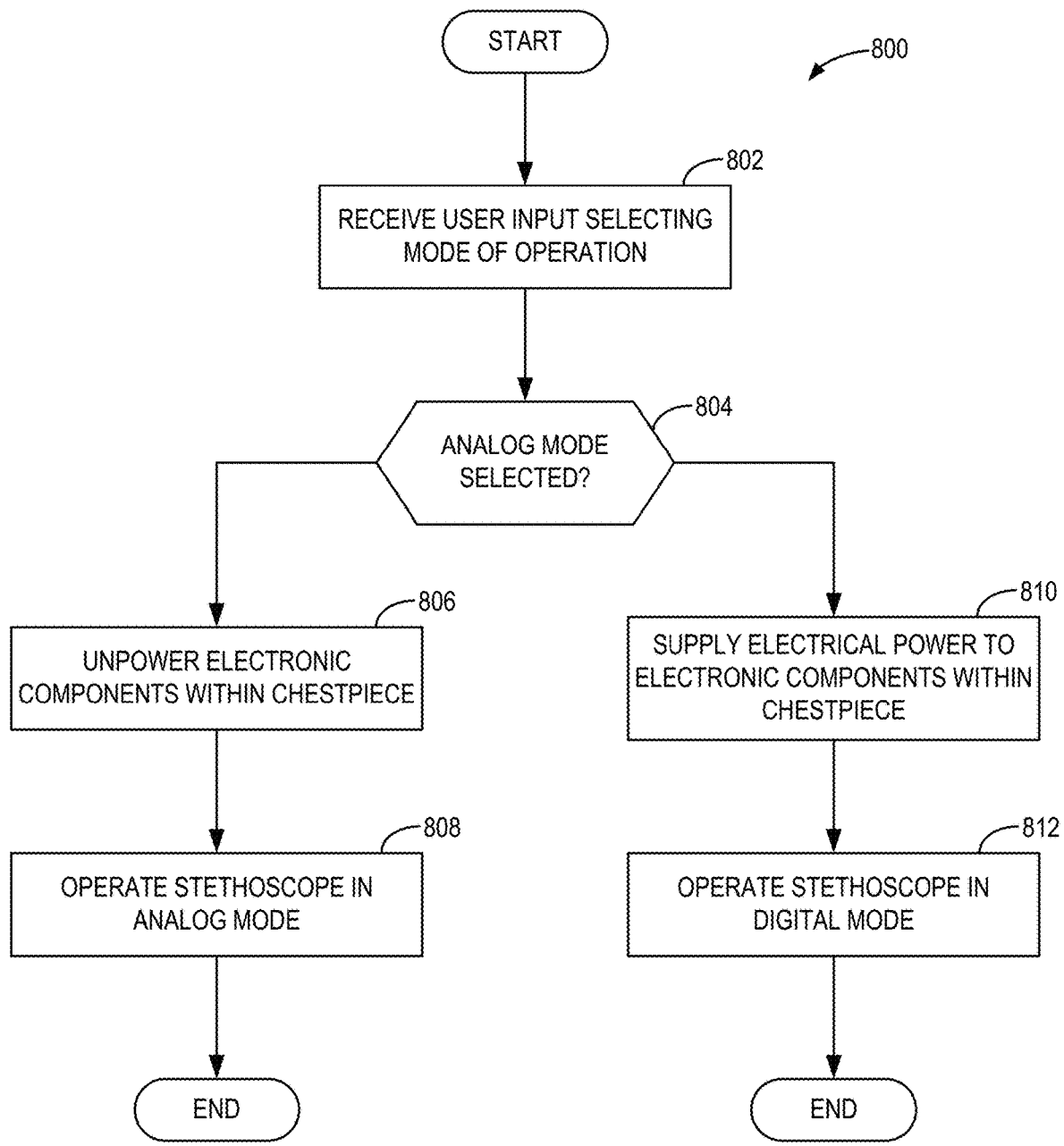
FIG. 8 is a flowchart illustrating a method of operation of the digital stethoscope.

Turning now to FIG. 8, a high-level flowchart illustrating a method 800 for operation of a hybrid analog-digital stethoscope is shown. The hybrid analog-digital stethoscope may be the electronic stethoscope 100 described herein that includes the chestpiece 110 with electronic components and the diaphragm 112. As described above, the chestpiece 110 is configured to connect to the output tube 106 via the connector 108, wherein the connector 108 includes the mode switching port 202 and the pathway 312. Thus, the method 800 is described herein with reference to FIGS. 1-7B, though it should be appreciated that the method may be applicable to other electronic stethoscopes without departing from the scope of this disclosure. At least portions of the method 800 may be performed via a human in cooperation with one or more of the systems of FIGS. 1-7B. In some examples, at least portions of method shown in FIG. 8 may be incorporated as executable instructions stored in non-transitory memory of a controller, for example a controller included as one of the electronic components within the chestpiece 110 (e.g., in the PCB and/or the CPU 116). In addition, some portions of the method may be performed via the controller transforming operating states of devices and actuators in the physical world.

At 802, the method 800 includes receiving a user input for a desired mode of operation of the electronic stethoscope. For example, the electronic stethoscope may be a hybrid device capable of operating both in digital mode and in analog (e.g., acoustic mode). In some examples, the user, via rotation of the connector with respect to the chestpiece (or the chestpiece with respect to the connector), may toggle between digital and analog mode. As described herein, the connector includes the mode switching port that when positioned in a first position, places the stethoscope in digital mode and when positioned in a second position, places the stethoscope in analog mode.

At 804, method 800 includes determining if analog mode of the electronic stethoscope is selected via the user input. In some examples, the determination of whether analog mode is selected may be based on output from a sensor, such as configuration sensor 130. For example, if the user has rotated or linearly translated the connector or chestpiece into the first position, digital mode may be selected and if the user has rotated or linearly translated the connector or chestpiece into the second position, analog mode may be selected. If analog mode is selected (YES at 804), method 800 proceeds to 806. If digital mode is selected (NO at 804), method 800 proceeds to 810.

At 806, method 800 includes unpowering the electronic components of the electronic stethoscope. For example, positioning the mode switching port in the analog configuration, an electrical connection between the power source (e.g., battery 124) and the electronic components may be severed. As an example, the mode switching port may include a component (e.g., a connector) on one side that when aligned in the first position for digital mode, connects the electronic components to the battery but when aligned in the second position for analog mode, does not connect the electronic components to the battery.

At 808, method 800 includes operating the electronic stethoscope in analog mode. As described herein, in analog mode, auscultation sounds detected by the diaphragm are transmitted into the pathway of the mode switching port and connector and then to the output tube and to the wearer via earpieces. With the mode switching port in the second position, the auscultated sounds may not pass through electronic components and thus may remain unmodified and undegraded by any damping or other effects the components themselves may have on the auscultated sounds.

At 810, when digital mode is selected, method 800 includes supplying electronic power to one or more electronic components of the electronic stethoscope. With the mode switching port in the first position with the pathway of the connector and mode switching port in acoustic communication with the electronic components, the component may connect the electronic components to the battery. For example, supplying electronic power to the one or more electronic components may be achieved with a sensor or a switch in line with the battery configured so that when the switching port is in the first position, electronic power may be provided to the one or more electronic components.

At 812, method 800 includes operating the stethoscope in the digital mode, wherein auscultation sounds are detected by the diaphragm, detected by the microphone within the chestpiece and converted to an electronic signal, processed by an electronic acoustic modifier (e.g., electronic acoustic modifier 120) for modification and amplification, and transmitted to the one or more speakers. The one or more speakers may output the modified acoustic signal as sound into the pathway of the mode switching port as the mode switching port is in acoustic communication with the one or more speakers.

In this way, in digital mode, the electronic components may be powered on so as to receive, modify, and output signals, and in analog mode, the electronic components may be powered off and auscultated sounds may be transmitted to the wearer similar to a traditional stethoscope.

The technical effect of the mechanism for switching between digital and analog mode in a hybrid analog-digital stethoscope is that a user may toggle between digital and analog mode as desired, for example based on battery state of charge. The mechanism mitigates any added bulk or weight to the device by incorporating the mechanism into existing components. By routing acoustic sounds in analog mode through the mode switching port, the sounds may avoid passing through the electronic components of the device. Thus, damping, amplification, or other unwanted modifications that would result from the effect of the mechanical characteristics of the electronic components on the auscultated sounds as the sounds pass through unpowered electronic components on their way to the wearer may be mitigated.

The disclosure also provides support for an electronic stethoscope, comprising: a chestpiece including a sound collecting interface and a plurality of electronic components, wherein the plurality of electronic components includes one or more microphones and one or more speakers, an output tube coupled to the chestpiece via a connector comprising a mode switching port, wherein the output tube, when the mode switching port is in a first position for digital mode, is in acoustic communication with the one or more speakers and, when the mode switching port is in a second position for analog mode, is in acoustic communication with the sound collecting interface. In a first example of the system, the chestpiece and the connector are configured to move relative to each other to switch between digital mode and analog mode. In a second example of the system, optionally including the first example, the chestpiece and the connector are configured to one of rotate relative to each other and move linearly relative to each other. In a third example of the system, optionally including one or both of the first and second examples in analog mode, the plurality of electronic components are powered off. In a fourth example of the system, optionally including one or more or each of the first through third examples, the system further comprises: a first acoustic channel acoustically connected to the one or more speakers and a second acoustic channel acoustically connected to the sound collecting interface. In a fifth example of the system, optionally including one or more or each of the first through fourth examples when the mode switching port is in the first position, the mode switching port is in acoustic communication with the first acoustic channel and is acoustically isolated from the second acoustic channel. In a sixth example of the system, optionally including one or more or each of the first through fifth examples when the mode switching port is in the second position, the mode switching port is in acoustic communication with the second acoustic channel and is acoustically isolated from the first acoustic channel. In a seventh example of the system, optionally including one or more or each of the first through sixth examples, the one or more microphones are configured to receive auscultated sound from the sound collecting interface and convert the auscultated sound into an electronic signal for output by the one or more speakers when the electronic stethoscope is in digital mode.

The disclosure also provides support for an electronic stethoscope device, comprising: a chestpiece including a diaphragm, one or more electronic components housed within the chestpiece, wherein the one or more electronic components comprise a microphone and a speaker, an output tube coupled to the chestpiece via a connector, wherein the connector includes an acoustic pathway therein that includes a first section in acoustic communication with the output tube and a second section in acoustic communication with one of the speaker and the diaphragm depending on a selected mode of the electronic stethoscope device, wherein: in digital mode, the acoustic pathway is in acoustic communication with the speaker, and in analog mode, the acoustic pathway is in acoustic communication with the diaphragm. In a first example of the system, the connector is configured to move within the chestpiece to switch between digital mode and analog mode. In a second example of the system, optionally including the first example, the acoustic pathway within the connector further comprises a third section, wherein the second section is in acoustic communication with the speaker in the digital mode and the third section is in acoustic communication with the diaphragm in the analog mode. In a third example of the system, optionally including one or both of the first and second examples, the one or more electronic components are powered on via a switch integrated with the connector when the electronic stethoscope device is in digital mode and are powered off via the switch when the electronic stethoscope device is in analog mode. In a fourth example of the system, optionally including one or more or each of the first through third examples, the system further comprises: a first acoustic channel acoustically connected directly to the speaker and a second acoustic channel acoustically connected directly to the diaphragm. In a fifth example of the system, optionally including one or more or each of the first through fourth examples in digital mode, the second section of the acoustic pathway of the connector is acoustically connected to the first acoustic channel and acoustically isolated from the second acoustic channel. In a sixth example of the system, optionally including one or more or each of the first through fifth examples in analog mode, the second section of the acoustic pathway of the connector is acoustically connected to the second acoustic channel and acoustically isolated from the first acoustic channel.

The disclosure also provides support for a method of operation of a hybrid analog-digital stethoscope, comprising: receiving user input selecting one of a digital mode and an analog mode, in response to selection of digital mode: receiving auscultated sound with a microphone detected via a diaphragm of a chestpiece, converting the auscultated sound to an electronic signal with the microphone, modifying the electronic signal with an electronic acoustic modifier, and outputting the electronic signal via a speaker to an output tube via an acoustic channel within a connector configured to acoustically connect the chestpiece to the output tube, wherein the acoustic channel is in acoustic communication with the speaker in digital mode, and in response to selection of analog mode: detecting auscultated sound with the diaphragm, and outputting the auscultated sound to the output tube via the acoustic channel within the connector, wherein the acoustic channel is in acoustic communication with the diaphragm in analog mode, wherein the user input comprises rotation of the connector with respect to the chestpiece, wherein the microphone and the speaker are housed within the chestpiece. In a first example of the method, the acoustic channel within the connector includes a mode switching port that when moved into a first position for digital mode acoustically couples to the speaker and when moved into a second position for analog mode acoustically couples to the diaphragm, wherein the connector is configured to move relative to the chestpiece via one of rotation and linear translation. In a second example of the method, optionally including the first example, the method further comprises:, in response to selection of digital mode, powering on electronic components including the microphone and the speaker. In a third example of the method, optionally including one or both of the first and second examples, the method further comprises:, in response to selection of analog mode, powering off electronic components including the microphone and the speaker. In a fourth example of the method, optionally including one or more or each of the first through third examples, modifying the electronic signal includes amplifying the electronic signal.

FIGS. 4-7B show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An electronic stethoscope, comprising:
a chestpiece including a sound collecting interface, a first acoustic channel, a second acoustic channel, and a plurality of electronic components, wherein the plurality of electronic components includes one or more microphones and one or more speakers;
an output tube coupled to the chestpiece via a connector comprising a mode switching port, wherein the output tube, when the mode switching port is in a first position for digital mode, is in acoustic communication with the one or more speakers via the first acoustic channel while the output tube is sealed off from the second acoustic channel, and, when the mode switching port is in a second position for analog mode, the output tube is in acoustic communication with the sound collecting interface via the second acoustic channel while the output tube is sealed off from the first acoustic channel, and wherein the first acoustic channel is acoustically isolated from the second acoustic channel.

2. The electronic stethoscope of claim 1, wherein the chestpiece and the connector are configured to move relative to each other to switch between digital mode and analog mode.

3. The electronic stethoscope of claim 2, wherein the chestpiece and the connector are configured to one of rotate relative to each other and move linearly relative to each other.

4. The electronic stethoscope of claim 1, wherein, in analog mode, the plurality of electronic components are powered off.

5. The electronic stethoscope of claim 1, wherein the one or more microphones and the one or more speakers are integrated into a PCB, and wherein the PCB is positioned on a side of the chestpiece opposite a diaphragm of the chestpiece.

6. The electronic stethoscope of claim 1, wherein, the first acoustic channel extends to a diaphragm of the chestpiece.

7. The electronic stethoscope of claim 1, further comprising a third acoustic channel positioned in the chestpiece, wherein the third acoustic channel extends from a diaphragm of the chestpiece to the one or more microphones.

8. The electronic stethoscope of claim 1, wherein the one or more microphones are configured to receive auscultated sound from the sound collecting interface and convert the auscultated sound into an electronic signal for output by the one or more speakers when the electronic stethoscope is in digital mode.

9. An electronic stethoscope device, comprising:
a chestpiece including a diaphragm;
one or more electronic components housed within the chestpiece, wherein the one or more electronic components comprise a microphone and a speaker, the speaker and the microphone positioned on a same wall of the chestpiece;
an output tube coupled to the chestpiece via a connector, wherein the connector includes an acoustic pathway therein that includes a first section in acoustic communication with the output tube and a second section in acoustic communication with one of the speaker and the diaphragm depending on a selected mode of the electronic stethoscope device, wherein:
in digital mode, the acoustic pathway is in acoustic communication with the speaker; and
in analog mode, the acoustic pathway is in acoustic communication with the diaphragm.

10. The electronic stethoscope device of claim 9, wherein the connector is configured to move within the chestpiece to switch between digital mode and analog mode.

11. The electronic stethoscope device of claim 9, wherein the acoustic pathway within the connector further comprises a third section, and wherein the second section is in acoustic communication with the speaker in the digital mode and the third section is in acoustic communication with the diaphragm in the analog mode.

12. The electronic stethoscope device of claim 9, wherein the one or more electronic components are powered on via a switch integrated with the connector when the electronic stethoscope device is in digital mode and are powered off via the switch when the electronic stethoscope device is in analog mode.

13. The electronic stethoscope device of claim 9, further comprising a first acoustic channel acoustically connected directly to the speaker and a second acoustic channel acoustically connected directly to the diaphragm.

14. The electronic stethoscope device of claim 13, wherein, in digital mode, the second section of the acoustic pathway of the connector is acoustically connected to the first acoustic channel and acoustically isolated from the second acoustic channel.

15. The electronic stethoscope device of claim 13, wherein, in analog mode, the second section of the acoustic pathway of the connector is acoustically connected to the second acoustic channel and acoustically isolated from the first acoustic channel.

16. A method of operation of a hybrid analog-digital stethoscope, comprising:
   receiving user input selecting one of a digital mode and an analog mode;
   in response to selection of the digital mode:
      receiving auscultated sound with a microphone detected via a diaphragm of a chestpiece, the chestpiece including a sound collecting interface, a first acoustic channel, a second acoustic channel, the microphone, and a speaker;
      converting the auscultated sound to an electronic signal with the microphone;
      modifying the electronic signal with an electronic acoustic modifier; and
      outputting the electronic signal via the speaker to an output tube via the first acoustic channel within a connector configured to acoustically connect the chestpiece to the output tube, wherein the first acoustic channel is in acoustic communication with the speaker in the digital mode while the output tube is sealed off from the second acoustic channel; and
   in response to selection of the analog mode:
      detecting auscultated sound with the diaphragm; and
      outputting the auscultated sound to the output tube via the second acoustic channel within the connector, wherein the second acoustic channel is in acoustic communication with the diaphragm in the analog mode while the output tube is sealed off from the first acoustic channel, wherein the first acoustic channel is acoustically isolated from the second acoustic channel, wherein the user input comprises rotation of the connector with respect to the chestpiece, and wherein the microphone and the speaker are housed within the chestpiece and positioned on a same wall of the chestpiece.

17. The method of claim 16, wherein the connector is configured to move relative to the chestpiece via one of rotation and linear translation.

18. The method of claim 16, further comprising, in response to selection of the digital mode, powering on electronic components including the microphone and the speaker.

19. The method of claim 16, further comprising, in response to selection of the analog mode, powering off electronic components including the microphone and the speaker.

20. The method of claim 16, wherein modifying the electronic signal includes amplifying the electronic signal.

* * * * *